US012758228B2

(12) United States Patent
Eldridge et al.

(10) Patent No.: US 12,758,228 B2
(45) Date of Patent: Oct. 13, 2026

(54) IMPLANTABLE EMBOLIZATION DEVICE

(71) Applicant: Medtronic, Inc., Minneapolis, MN (US)

(72) Inventors: Amanda K. Eldridge, Seattle, WA (US); Jeffrey H. Vogel, Brooklyn Park, MN (US); Victoria Schuman, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 728 days.

(21) Appl. No.: 17/812,069

(22) Filed: Jul. 12, 2022

(65) Prior Publication Data

US 2024/0016497 A1 Jan. 18, 2024

(51) Int. Cl.
*A61B 17/12* (2006.01)

(52) U.S. Cl.
CPC .. *A61B 17/12145* (2013.01); *A61B 17/12109* (2013.01); *A61B 17/12113* (2013.01); *A61B 17/1214* (2013.01); *A61B 17/1215* (2013.01)

(58) Field of Classification Search
CPC ........ A61B 17/12145; A61B 17/12109; A61B 17/1215; A61B 17/12113; A61B 17/1214
See application file for complete search history.

(56) References Cited

U.S. PATENT DOCUMENTS

| | | | |
|---|---|---|---|
| 5,649,949 | A | 7/1997 | Wallace et al. |
| 5,690,667 | A | 11/1997 | Gia |
| 5,733,329 | A | 3/1998 | Wallace et al. |
| 5,800,454 | A | 9/1998 | Jacobsen |
| 6,033,423 | A | 3/2000 | Ken et al. |
| 6,063,100 | A | 5/2000 | Diaz et al. |
| 6,117,157 | A | 9/2000 | Tekulve |
| 6,156,061 | A | 12/2000 | Wallace et al. |
| 6,179,857 | B1 | 1/2001 | Diaz et al. |
| 6,432,134 | B1 | 8/2002 | Anson et al. |
| 6,551,340 | B1 | 4/2003 | Konya et al. |

(Continued)

FOREIGN PATENT DOCUMENTS

| | | | |
|---|---|---|---|
| EP | 0964648 | A1 | 12/1999 |
| WO | 0193937 | A2 | 12/2001 |

(Continued)

OTHER PUBLICATIONS

International Search Report and Written Opinion mailed Sep. 29, 2023, International Application No. PCT/US2023/069998, 14 pages.

*Primary Examiner* — Jing Rui Ou
(74) *Attorney, Agent, or Firm* — Fortem IP LLP

(57) ABSTRACT

Devices, systems, and methods for occluding body lumens are disclosed herein. According to some embodiments, the present technology includes an embolization device configured to be positioned within a body lumen of a patient. The embolization device can comprise an elongated primary structure formed of a coiled wire, where the primary structure forms a secondary structure when unconstrained in which the primary structure forms an anchor portion and a trailing portion. The anchor portion can be configured to anchor the embolization device at the treatment site, and the trailing portion can be configured to fill space in the body lumen to reduce or block flow into or through the body lumen. The primary structure can have a stiffening feature along at least a portion of the anchor portion.

20 Claims, 8 Drawing Sheets

(56) References Cited

U.S. PATENT DOCUMENTS

| | | | |
|---|---|---|---|
| 6,602,269 | B2 | 8/2003 | Wallace et al. |
| 6,605,101 | B1 | 8/2003 | Schaefer et al. |
| 6,635,069 | B1 | 10/2003 | Teoh et al. |
| 6,790,218 | B2 | 9/2004 | Jayaraman |
| 6,860,893 | B2 | 3/2005 | Wallace et al. |
| 7,029,486 | B2 | 4/2006 | Schaefer et al. |
| 7,033,374 | B2 | 4/2006 | Schaefer et al. |
| 7,300,661 | B2 | 11/2007 | Henson et al. |
| 7,485,123 | B2 | 2/2009 | Porter |
| 7,488,332 | B2 | 2/2009 | Teoh et al. |
| 7,645,292 | B2 | 1/2010 | Porter |
| 7,879,064 | B2 | 2/2011 | Monstadt et al. |
| 8,007,509 | B2 | 8/2011 | Buiser et al. |
| 8,043,321 | B2 | 10/2011 | Elliott |
| 8,066,036 | B2 | 11/2011 | Monetti et al. |
| 8,152,839 | B2 | 4/2012 | Buiser et al. |
| 8,226,660 | B2 | 7/2012 | Teoh et al. |
| 8,308,751 | B2 | 11/2012 | Gerberding |
| 8,323,306 | B2 | 12/2012 | Schaefer et al. |
| 8,414,634 | B2 | 4/2013 | Sekido et al. |
| 8,910,501 | B2 | 12/2014 | Gorospe et al. |
| 9,011,480 | B2 | 4/2015 | Divino et al. |
| 9,055,948 | B2 | 6/2015 | Jaeger et al. |
| 9,089,405 | B1 | 7/2015 | Gulachenski et al. |
| 9,301,764 | B2 | 4/2016 | White et al. |
| 9,533,344 | B2 | 1/2017 | Monetti et al. |
| 9,615,833 | B2 | 4/2017 | Suzuki et al. |
| 9,636,118 | B2 | 5/2017 | Garza et al. |
| 9,713,475 | B2 | 7/2017 | Divino et al. |
| 9,795,389 | B2 | 10/2017 | Elliott |
| 9,844,382 | B2 | 12/2017 | Aboytes et al. |
| 9,980,734 | B2 | 5/2018 | Le et al. |
| 9,993,252 | B2 | 6/2018 | Keeley et al. |
| 10,058,330 | B2 | 8/2018 | Fitz et al. |
| 10,081,048 | B2 | 9/2018 | Monetti et al. |
| 10,098,645 | B2 | 10/2018 | Le et al. |
| 10,111,670 | B2 | 10/2018 | Lorenzo et al. |
| 10,136,897 | B2 | 11/2018 | Watson et al. |
| 10,182,822 | B2 | 1/2019 | Freudenthal |
| 10,290,230 | B2 | 5/2019 | Babiker et al. |
| 10,299,798 | B2 | 5/2019 | Le et al. |
| 10,307,168 | B2 | 6/2019 | Morita |
| 10,342,548 | B2 | 7/2019 | Duncan |
| 10,548,606 | B2 | 2/2020 | Hui et al. |
| 10,595,875 | B2 | 3/2020 | Mayer et al. |
| 10,603,043 | B2 | 3/2020 | Barkenbus et al. |
| 10,688,550 | B2 | 6/2020 | Suzuki |
| 10,709,453 | B2 | 7/2020 | Suzuki |
| 10,736,758 | B2 | 8/2020 | Ruvalcaba et al. |
| 10,751,065 | B2 | 8/2020 | Soto Del Valle et al. |
| 10,808,341 | B2 | 10/2020 | Köppe |
| 10,842,607 | B2 | 11/2020 | Bowman et al. |
| 10,857,589 | B2 | 12/2020 | Monetti et al. |
| 10,893,868 | B2 | 1/2021 | Divino et al. |
| 2002/0052613 | A1* | 5/2002 | Ferrera ............ A61B 17/12145 606/157 |
| 2004/0034378 | A1* | 2/2004 | Monstadt ......... A61B 17/12145 606/157 |
| 2004/0059370 | A1 | 3/2004 | Greene et al. |
| 2004/0098023 | A1 | 5/2004 | Lee et al. |
| 2005/0090856 | A1 | 4/2005 | Porter |
| 2005/0107823 | A1 | 5/2005 | Leone et al. |
| 2006/0095071 | A1 | 5/2006 | Zhang |
| 2006/0100661 | A1 | 5/2006 | Jaeger et al. |
| 2006/0200190 | A1 | 9/2006 | Lorenzo et al. |
| 2011/0245861 | A1* | 10/2011 | Chen ................ A61B 17/12154 606/200 |
| 2012/0089174 | A1* | 4/2012 | Chen .................. A61B 17/1219 606/200 |
| 2013/0184658 | A1 | 7/2013 | Duncan |
| 2014/0128907 | A1* | 5/2014 | Hui ......................... B29C 65/00 156/196 |
| 2015/0182226 | A1 | 7/2015 | Teoh |
| 2015/0257765 | A1 | 9/2015 | Barkenbus et al. |
| 2015/0297238 | A1 | 10/2015 | Ken |
| 2016/0228127 | A1 | 8/2016 | Zhang et al. |
| 2017/0035436 | A1 | 2/2017 | Morita |
| 2017/0086852 | A1 | 3/2017 | Martinez et al. |
| 2017/0189033 | A1 | 7/2017 | Sepetka et al. |
| 2018/0036012 | A1 | 2/2018 | Aboytes et al. |
| 2018/0104040 | A1 | 4/2018 | Bowman et al. |
| 2018/0263630 | A1 | 9/2018 | Tsukumo |
| 2018/0263633 | A1 | 9/2018 | Tsukumo |
| 2018/0271533 | A1 | 9/2018 | Le et al. |
| 2018/0303486 | A1 | 10/2018 | Rosenbluth et al. |
| 2019/0015108 | A1 | 1/2019 | Maitland et al. |
| 2019/0046210 | A1 | 2/2019 | Bowman |
| 2019/0209181 | A1 | 7/2019 | Mayer et al. |
| 2019/0298387 | A1 | 10/2019 | Qin et al. |
| 2019/0307546 | A1 | 10/2019 | Aguilar et al. |
| 2019/0374228 | A1 | 12/2019 | Wallace et al. |
| 2020/0060689 | A1 | 2/2020 | Andrews et al. |
| 2020/0069311 | A1 | 3/2020 | Cruise et al. |
| 2020/0138422 | A1 | 5/2020 | Hebert et al. |
| 2020/0138446 | A1 | 5/2020 | Jockenhoevel et al. |
| 2020/0197017 | A1 | 6/2020 | Hamel et al. |
| 2020/0360025 | A1 | 11/2020 | Wallace et al. |
| 2021/0045749 | A1 | 2/2021 | Wang et al. |

FOREIGN PATENT DOCUMENTS

| | | |
|---|---|---|
| WO | 2018053314 A1 | 3/2018 |
| WO | 2018073830 A2 | 4/2018 |

* cited by examiner

IMPLANTABLE EMBOLIZATION DEVICE

TECHNICAL FIELD

The present technology relates to implantable medical devices configured for embolizing a vascular site.

BACKGROUND

Implantable embolization devices may be used to embolize, e.g., occlude, a vascular site. Possible clinical applications include controlling bleeding from hemorrhages, reducing blood flow to tumors, and treating a diverse number of conditions including, for example, pathologies of the brain, the heart, and the peripheral vascular system. Among other examples, implantable embolization devices may be used to treat aneurysms, vascular malformations, arteriovenous fistulas, pelvic congestion syndrome, and varicoceles. An implantable embolization device may be configured to pack a vascular site in a patient, thereby reducing blood flow, promoting clotting, and eventually occluding the vascular site.

SUMMARY

Embolization devices are used in a wide range of clinical applications to block blood flow to distal vasculature. In large- or high-flow vessels, or during extravasation, high blood flow rates can make anchoring the device relative to the vessel or body lumen difficult. As detailed below, the embolization devices of the present technology include an anchor portion and one or more stiffening features at the anchor portion or other portions of the device that provide improved anchoring relative to devices without such stiffening features. The subject technology is illustrated, for example, according to various aspects described below, including with reference to FIGS. 1A-8C. Various examples of aspects of the subject technology are described as numbered clauses (1, 2, 3, etc.) for convenience. These are provided as examples and do not limit the subject technology.

1. An embolization device configured to be positioned within a body lumen of a patient, the embolization device comprising:
   - an elongated primary structure formed of a coiled wire defining a lumen therethrough, wherein the primary structure forms a secondary structure when unconstrained in which the primary structure forms an anchor portion and a trailing portion, and wherein:
     - the anchor portion comprises at least one loop configured to be in contact with and press radially outwardly against an inner surface of the body lumen at a treatment site such that the anchor portion is configured to anchor the embolization device at the treatment site, and
     - the trailing portion is configured to fill space in the body lumen to reduce or block flow into or through the body lumen, wherein the trailing portion is more flexible than the anchor portion, and
   - wherein the primary structure has a first length corresponding to the trailing portion and a second length corresponding to the anchor portion, and wherein the primary structure comprises a filler material disposed within the lumen of the primary structure along at least a portion of the second length.

2. The embolization device of Clause 1, wherein the filler material is disposed within the lumen of the primary structure along the entire second length of the primary structure.

3. The embolization device of Clause 1, wherein the anchor portion comprises a first loop and a second loop contiguous with the first loop, and wherein the filler material is disposed within the lumen of the primary structure along one or both of the first loop and the second loop.

4. The embolization device of any one of Clauses 1 to 3, wherein the embolization device is configured to be positioned within a blood vessel.

5. The embolization device of Clause 4, wherein the trailing portion comprises a first portion and a second portion, wherein the first portion comprise a three-dimensional structure in the unconstrained state that is configured to receive at least a portion of the second portion therein.

6. The embolization device of any one of Clauses 1 to 3, wherein the embolization device is configured to be positioned within an aneurysm.

7. An embolization device configured to be positioned within a body lumen of a patient, the embolization device comprising:
   - an elongated primary structure having a sidewall formed of a coiled wire, wherein the primary structure forms a secondary structure when unconstrained in which the primary structure forms an anchor portion and a trailing portion, and wherein:
     - the anchor portion comprises at least one loop configured to be in contact with and press radially outwardly against an inner surface of the body lumen at a treatment site such that the anchor portion is configured to anchor the embolization device at the treatment site, and
     - the trailing portion is configured to fill space in the body lumen to reduce or block flow into or through the body lumen, wherein the trailing portion is more flexible than the anchor portion, and
   - wherein the primary structure has a first length corresponding to the trailing portion and a second length corresponding to the anchor portion, and wherein the sidewall of the primary structure comprises a first number of coil layers along the first length and a second number of coil layers along at least a portion of the second length, the second number greater than the first number.

8. The embolization device of Clause 7, wherein the second number of coil layers extends along the entire second length of the primary structure.

9. The embolization device of Clause 7, wherein the anchor portion comprises a first loop and a second loop contiguous with the first loop, and wherein the second number of coil layers extends along one or both of the first loop and the second loop.

10. The embolization device of any one of Clauses 7 to 9, wherein the first number of coil layers is one coil layer and the second number of coil layers is two coil layers.

11. The embolization device of any one of Clauses 7 to 10, wherein the sidewall of the primary structure comprises an outer coil and an inner coil along at least a portion of the second length, and only the outer coil along the first length.

12. The embolization device of Clause 11, wherein the outer coil and inner coil are formed of the same wire.

13. The embolization device of Clause 11, wherein the outer coil and inner coil are formed of different wires.

14. The embolization device of any one of Clauses 11 to 13, wherein the outer coil is wound in a first direction and the inner coil is wound in a second direction opposite the first direction.

15. The embolization device of any one of Clauses 11 to 13, wherein the outer coil and inner coil are wound in the same direction.

16. The embolization device of any one of Clauses 7 to 15, wherein the embolization device is configured to be positioned within a blood vessel.

17. The embolization device of Clause 16, wherein the trailing portion comprises a first portion and a second portion, wherein the first portion comprise a three-dimensional structure in the unconstrained state that is configured to receive at least a portion of the second portion therein.

18. The embolization device of any one of Clauses 7 to 15, wherein the embolization device is configured to be positioned within an aneurysm.

19. An embolization device configured to be positioned within a body lumen of a patient, the embolization device comprising:

an elongated primary structure formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the wire comprises a first length having a first cross-sectional dimension and a second length comprising a second cross-sectional dimension greater than the first cross-sectional dimension, and wherein the first length of the wire extends along at least a portion of a length of the primary structure that forms the anchor portion and the second length of the wire extends along a length of the primary structure that forms the trailing portion.

20. The embolization device of Clause 19, wherein the second length of the wire extends along the entire portion of the length of the primary structure that forms the anchor portion.

21. The embolization device of Clause 19, wherein the anchor portion comprises a first loop and a second loop contiguous with the first loop, and wherein the second length of the wire extends along one or both of the first loop and the second loop.

22. The embolization device of any one of Clauses 19 to 21, wherein the embolization device is configured to be positioned within a blood vessel.

23. The embolization device of any one of Clauses 19 to 22, wherein the embolization device is configured to be positioned within an aneurysm.

24. An embolization device configured to be positioned within a body lumen of a patient, the embolization device comprising:

an elongated primary structure having a sidewall formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the primary structure has a first length corresponding to the trailing portion and a second length corresponding to the anchor portion, and wherein the sidewall of the primary structure comprises a first number of coil layers along the first length and a second number of coil layers along at least a portion of the second length, the second number greater than the first number, and wherein the wire comprises a first wire length having a first cross-sectional dimension and a second wire length comprising a second cross-sectional dimension greater than the first cross-sectional dimension, and wherein the first wire length extends along at least a portion of the second length of the primary structure and the second wire length of the wire extends along the first length of the primary structure.

25. An embolization device configured to be positioned within a body lumen of a patient, the embolization device comprising:

an elongated primary structure formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the primary structure has a first length corresponding to the trailing portion and a second length corresponding to the anchor portion, and wherein the primary structure comprises a filler material disposed within the lumen of the primary structure along at least a portion of the second length, and wherein the wire comprises a first wire length having a first cross-sectional dimension and a second wire length comprising a second cross-sectional dimension greater than the first cross-sectional dimension, and wherein the first wire length extends along at least a portion of the second length of the primary structure and the second wire length extends along the first length of the primary structure.

26. An embolization device configured to be positioned within a body lumen of a patient, the embolization device comprising:

an elongated primary structure formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the primary structure has a first length corresponding to the trailing portion and a second length corresponding to the anchor portion, and wherein the sidewall of the primary structure comprises a first number of coil layers along the first length and a second number of coil layers along at least a portion of the second length, the second number greater than the first number wherein the primary structure has a first length corresponding to the trailing portion and a second length corresponding to the anchor portion, and wherein the primary structure comprises a filler material disposed within the lumen of the primary structure along at least a portion of the second length.

27. An embolization device configured to be positioned within a body lumen of a patient, the embolization device comprising:

an elongated primary structure formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the primary structure has a first length corresponding to the trailing portion and a second length corresponding to the anchor portion, and wherein the sidewall of the primary structure comprises a first number of coil layers along the first length and a second number of coil layers along at least a portion of the second length, the second number greater than the first number, and wherein the primary structure comprises a filler material disposed within the lumen of the primary structure along at least a portion of the second length, and wherein the wire comprises a first wire length having a first cross-sectional dimension and a second wire length comprising a second cross-sectional dimension greater than the first cross-sectional dimension, and wherein the first wire length extends along at least a portion of the second length of the primary structure and the second wire length extends along the first length of the primary structure.

28. A system, comprising:

any of the embolization devices of Clauses 1 to 27; and a catheter having a proximal end portion configured to be extracorporeally positioned and a distal end portion configured to be intravascularly delivered to a treatment site within a blood vessel, wherein the embolization device is loaded into the catheter in an elongated configuration in which the anchor portion is distal of the trailing portion such that the anchor portion is delivered to the treatment site before the trailing portion.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
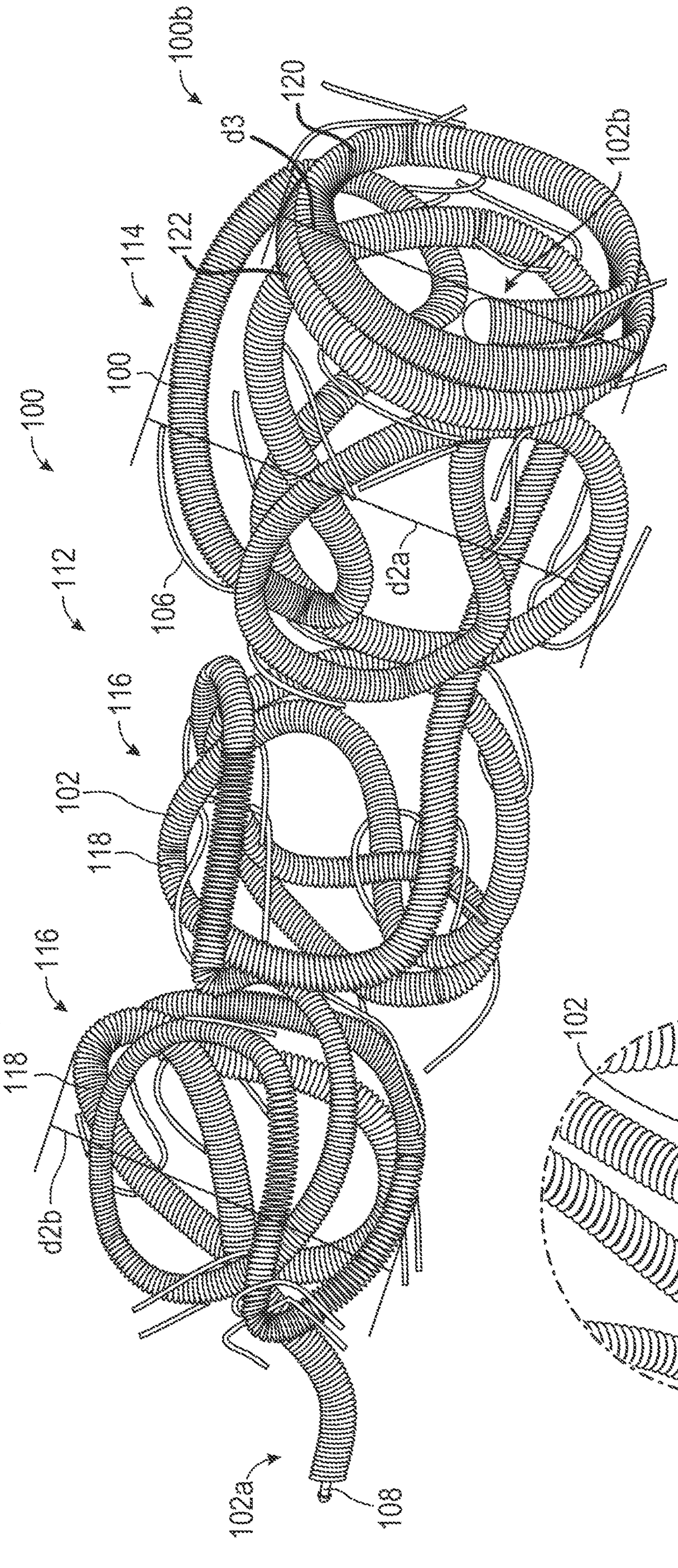
FIG. 1A is a perspective view illustrating an embolization device configured in accordance with several embodiments of the present technology.

The present technology is directed to implantable embolization devices configured for embolizing a site within the vasculature of a patient or for use in another body lumen. The embolization devices disclosed herein may be configured to pack a body lumen in a patient, thereby reducing blood or other fluid flow at or within the body lumen. The embolization devices herein can be used to, for example, occlude a blood vessel (e.g., a peripheral vessel) and sacrifice the blood vessel. While a blood vessel is primarily referred to herein, the example embolization devices of the present technology may be used in other hollow anatomical structures or other vascular sites, such as aneurysms. The embolization devices of the present technology can be used to embolize and/or takedown any portion of the vasculature (e.g., any vein, artery, or aneurysm). Non-limiting examples include any peripheral artery or vein, a splenic artery or vein, a hepatic artery or vein, an iliac artery or vein, a gastroduodenal artery or vein, a cerebral aneurysm, a peripheral aneurysm, an ovarian artery or vein, a renal artery or vein, a portal vein aneurysm, and/or a spermatic artery or vein.

Embolization devices are used in a wide range of clinical applications to block blood flow to distal vasculature. In large- or high-flow vessels, or during extravasation, high blood flow rates can make anchoring the device relative to the vessel or body lumen difficult. Occlusion techniques for high-flow scenarios can include the use of a single large, stiff coil, a plurality of coils to create a backstop, or a plug, each of which come with several disadvantages. For instance, a single large, stiff coil may anchor, but will likely not contribute much to occluding the vessel. As a result, additional filler coils must be introduced, thereby adding time to the procedure. Using a plurality of coils comes with similar challenges. Plugs typically require a larger catheter to deliver, and it is not always feasible to navigate to the treatment site with a larger catheter. Also, plugs require a longer landing zone than a coil, and in some cases the tortuosity of the vessel may be too great to permit landing a plug successfully.

As detailed below, the embolization devices of the present technology include an anchor portion and one or more stiffening features at the anchor portion or other portions of the device that provide improved anchoring relative to devices without such stiffening features. High-flow scenarios where the enhanced anchor strength of the present technology may be especially useful can include, but are not limited to, embolization for the following conditions: splenic artery aneurysm or vessel takedown, internal iliac aneurysm or vessel takedown, hepatic artery aneurysm or vessel takedown, peripheral arteriovenous malformations, pulmonary arteriovenous malformations, inferior mesenteric artery aneurysm or vessel takedown, portal vein aneurysm or vessel takedown, renal artery aneurysm or vessel takedown.

The embolization devices described herein have an elongated primary structure such as, for example, a linear wire or a coiled wire. In those embodiments in which the primary structure comprises a coiled wire, the wire defining the coiled wire is referred to as the "base structure." Once deployed at the vascular site, the embolization device assumes a secondary configuration or shape, also referred to herein as a deployed configuration or a deployed shape. In the deployed configuration, the device can include at least two portions, each defining a distinct three-dimensional ("3D") structure. As detailed below, the device can include at least a trailing portion and an anchor portion. The anchor portion can be at or near the leading end of the primary structure and secondary structure and comprise multiple types of 3D structures or may comprise only a single 3D structure. The trailing portion can comprise multiple types of 3D structures (such as the first and second portions, described below) or may comprise only a single 3D structure. In any case, the 3D structures may define one or more loops, or may define relatively complex 3D shapes, such as loops in various sizes and orientations relative to each other. The orientation of the loops of a given 3D structure can be, for example, polyhedral, such as a tetrahedron, a hexahedron, an octahedron, or the like. The incorporation of multiple types of 3D structures may provide added features or benefits when compared with an embolization device without multiple 3D structures. As an example, an embolization device with multiple 3D structures may include some such structures that are configured to anchor the device at a vascular site and other structures that are configured to pack in and more completely block the site.

The base structure may vary along or between different portions of the device and/or along the length of the base structure to impart one or more structural characteristics. For example, the base structure can have one or more stiffening features, such as a varied diameter along its length and other features described below. Additionally or alternatively, the primary structure may vary along or between different portions of the device and/or along the length of the primary structure to impart one or more structural characteristics. For example, the primary structure can have one or more stiffening features, such as a filler at certain portions along its length, a varied diameter along its length, a varied pitch along its length, a varied number of layers along its length, and others described below.

A catheter delivery system is often used to place an implantable embolization device at a vascular site within a patient. A delivery system can sometimes include, for example, a catheter configured to be delivered to the target body lumen over a guidewire, and a positioning element (e.g., a push member, optionally with a detachment mechanism that connects to the primary structure) that advances the embolization device out of a lumen of the catheter to the body lumen. Once positioned, the embolization device is detached from the delivery system. The embolization device may be configured to pack (e.g., fill or otherwise occupy a space through which blood flows) the body lumen thereby reducing blood flow, promoting clotting, and eventually occluding the body lumen.

In many cases the embolization devices may exhibit different shapes depending on its surrounding environment. The different shapes can, in some cases, include a primary shape as an embolization device is delivered through the narrow confines of a catheter, and a secondary shape once deployed at a vasculature site. As an example, an embolization device may have a longitudinally extending shape as it is advanced through a catheter. Upon exiting the catheter, the device may take on a secondary shape (e.g., defining a greater cross-sectional dimension than the primary shape) within the vasculature or body lumen. For example, the embolization device may exhibit a secondary shape designed to pack the cross-section of the vascular site more completely.

In some examples the trailing portion of the embolization device comprises one or more first portions and one or more second portions, each portion having a deployed configuration that defines a 3D structure formed from one or more loops of the elongated primary structure of the device. The deployed configuration of the one or more first portions is configured to anchor the embolization device in the body lumen of the patient and/or create a space for the second portion to be deployed into, while the deployed configurations of the one or more second portions are configured to block the vessel lumen. The loop(s) forming the first portion may in some cases be referred to as anchoring loops and may be slightly larger than the nominal vessel size for which the embolization device is designed. The first portion may also be helpful in anchoring the embolization device within more elastic vessels, such as some veins, that may expand to a relatively large size. The first portion may additionally be helpful in compensating for sizing errors from clinicians underestimating the sizing of the target vasculature. In some embodiments, all or a portion of the first portion can include one or more of the stiffening features disclosed herein.

The deployed configurations of the second portions may have a maximum cross-sectional dimension (e.g., a diameter or width) that is smaller than the maximum cross-sectional dimension of the deployed configuration of the first portion. For example, 3D structures of the second portions may be formed from loops, in some cases referred to as packing loops, that are designed to more easily pack in the space created at the embolization site by an anchoring 3D structure. For example, the second portion may be deployed at least partially (e.g., partially or fully) within the first portion. Each second portion can be configured to deploy into a smaller volume than the first portion. The deployed volume of the first portion or the second portion may be a function of the respective maximum cross-sectional dimension.

In some examples, the trailing portion does not comprise multiple portions and/or multiple distinct 3D structures.

The anchor portion can have a shape in a deployed configuration that is configured to anchor the embolization device within the patient's vasculature. As detailed herein, all or a portion of the anchor portion can have one or more stiffening features that impart greater rigidity to the anchor portion than the rest of the primary structure and/or secondary structure. In some embodiments, the anchor portion comprises one or more loops of the elongated primary structure. In those embodiments in which the anchor portion comprises two or more loops, the loops may be helical in nature. In some examples one or more of the helical loops may have a maximum cross-sectional dimension that is slightly larger than the nominal vessel size for which the device is designed. In some examples, the diameter of the one or more loops may be approximately the same as the maximum cross-sectional dimension of the deployed configuration of the first portion(s). In some examples, one or more of the loops of the anchor portion may have a maximum cross-sectional dimension that is smaller than the nominal vessel size for which the device is designed. Accordingly, the deployed configuration of the anchor portion may be configured to help ensure that the loops of the primary structure assume a deployed configuration, rather than an elongated configuration, upon exiting the delivery system. In some examples some or all of the loops of the anchor portion may have a tapered configuration, in which the loops' diameters increase from one end toward the other end.

In those embodiments in which the trailing portion includes first and second portions, the anchor portion of the device may be closest to the first portion, and opposite the first portion from the second portion (along the primary structure). Accordingly, the order of the portions may extend from the second portion(s) at a trailing end of the primary structure to the first portion to the anchor portion at the leading end.

FIG. 1A is a perspective view illustrating an implantable embolization device 100 (or "device 100") configured to embolize a site in a body lumen of a patient. The device 100 has a proximal end portion 100*a* and a distal end portion 100*b*. FIG. 1A depicts the embolization device 100 in a secondary configuration that includes multiple 3D structures, which in some cases may also be referred to as complex shapes, configurations, or structures. The secondary configuration shown in FIG. 1A may represent the configuration of the device 100 in its relaxed state with no external forces being applied to the device 100.

Figure 1B:
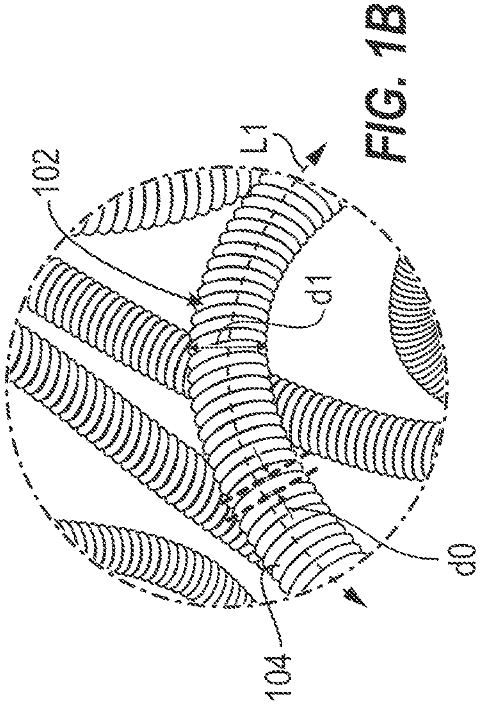
FIG. 1B is an enlarged view of a portion of the embolization device shown in FIG. 1A, configured in accordance with several embodiments of the present technology.

The embolization device 100 includes a primary structure 102 that is shaped to produce the deployed configuration illustrated in FIG. 1A. The primary structure 102 can have a cross-sectional dimension d1 (see FIG. 1B), a trailing end 102*a*, a leading end 102*b*, and a longitudinal axis L1 (see FIG. 1B) extending therebetween. In some examples, the primary structure 102 may be a wire or other filamentous material, or a tube. In some examples, including that shown in FIG. 1A, the primary structure 102 may be a length of coiled material. For example, FIG. 1B shows an enlarged view of a portion of the device 100 in which the primary structure 102 is a length of coil formed from many windings or turns of a base structure 104, such as a wire or other suitable material. In some embodiments, the primary structure 102 defines a lumen extending therethrough. In some examples, the primary structure 102 may also incorporate other elements to assist in the function of a detachable embolization device, such as a detachment element 108 and/or a stretch-resistant elements (not shown) extending through a lumen of the primary structure 102. As illustrated in FIG. 1A, in some embodiments the device 100 can optionally include one or more occlusive members 106 incorporated into and/or disposed on the base structure 104 and/or primary structure 102. The occlusive members 106 can be threads, strands, wires, coils, or other occlusive elements that increase the effective surface area of the device 100. In some embodiments the embolization device 100 does not include any occlusive members 106.

Figure 2:
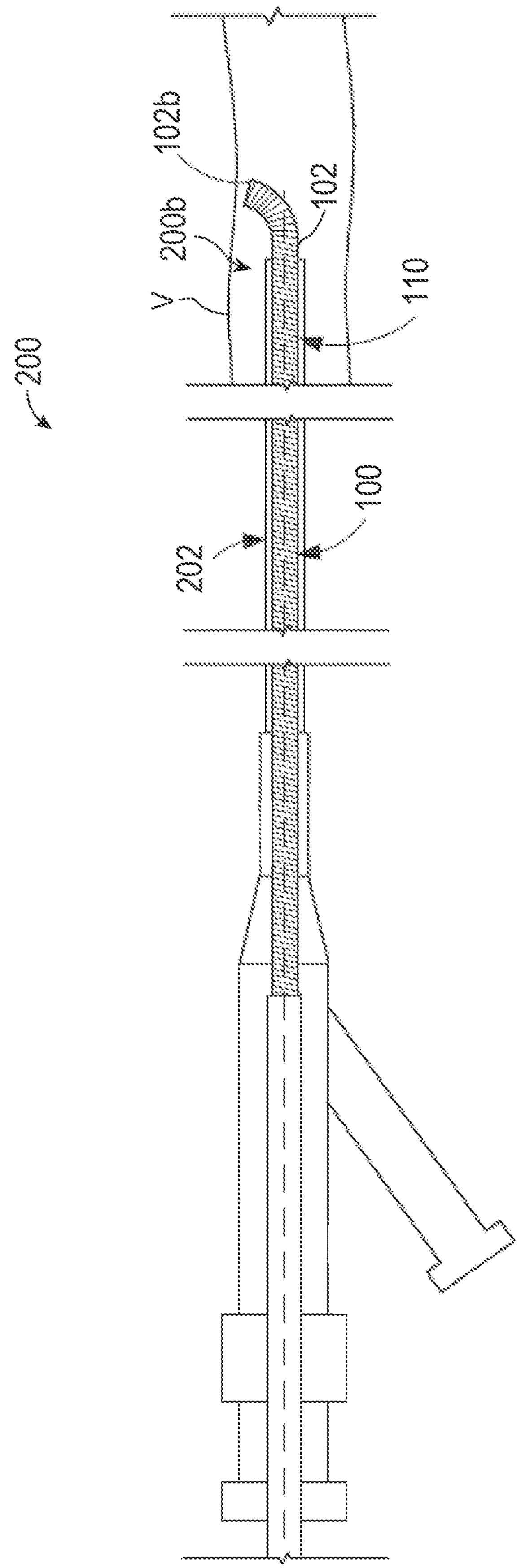
FIG. 2 is a side view of an embolization device of the present technology positioned within a delivery device.

Referring to FIG. 2, the embolization device 100 can have a delivery configuration (also referred to as a primary configuration or primary shape) in which the primary structure 102 has a primary shape that is configured to fit within an inner lumen 202 of a catheter 200 for delivering the device 100 to a treatment site in a body lumen. In such cases the primary shape may be, for example, a longitudinal or lengthwise extension of the primary structure 102. In some examples, the embolization device 100 has a delivery configuration that is a substantially linear configuration within the inner lumen of the catheter. As the device 100 is deployed from the inner lumen 202 into a body lumen, the primary structure 102 exits the catheter and assumes its secondary configuration (see, for example, the structure shown in FIG. 1A and FIG. 3).

Returning to FIG. 1A, the embolization device 100 can include an anchor portion 110 and a trailing portion 112, the trailing portion 112 comprising one or more first portions 114 and one or more second portions 116. In some embodiments, the trailing portion 112 comprises only first portions 114, only second portions 116, or another 3D structure(s). Although one first portion 114 is shown in FIG. 1A, in other examples the embolization device 100 can include any suitable number of first portions 114, such as zero or two or more. Likewise, although two second portions 116 are shown in FIG. 1A, in other examples, the embolization device 100 can include any suitable number of second portions 116, such as zero, one, or three or more.

In the deployed configuration of FIG. 1A, each of the first and second portions 114, 116 include multiple loops 118 of the primary structure 102 that form a separate 3D structure for each of the portions 114, 116. The loops 118 forming the first portion 114 may be described as first loops herein, while loops 118 forming each second portion 116 may be described as second loops. In some examples, the 3D structure of the first portion 114 is configured to frame a space in a body lumen of a patient for filling by the second portion 116 and the 3D structures of the second portions 116 are configured to pack a vascular site (e.g., a vessel lumen or an aneurysm sac) to occlude or embolize the vascular site. Accordingly, in some cases the loops 118 forming the deployed structure of the first portion 114 may be referred to as "framing" loops and the loops forming the deployed structure of the second portions 116 may be referred to as "packing" or "filling" loops. As an example, the deployed first portion 114 may define scaffolding and the one or more second portions 116 may be configured to fit within and pack the scaffolding, such that the one or more second portions 116 tuck into the first portion 114. An example of this deployed configuration is shown in FIGS. 4D and 4E.

The first portion 114 has a maximum cross-sectional dimension d2a, each second portion 116 has a maximum cross-sectional dimension d2b, and the anchor portion 110 has a maximum cross-sectional dimension d3. The maximum cross-sectional dimension d2b of each second portion 116 can be smaller than the maximum cross-sectional dimension d2a of the first portion 114. As a result, each second portion 116 is configured to deploy into a smaller volume than the first portion 114. In some cases, as discussed below, the maximum cross-sectional dimension d2a of the first portion 114 and/or anchor portion 110 is selected based on the size of the vessel in which the device 100 is intended to be used, and the size of the maximum cross-sectional dimension d2b of each second portion 116 is selected based on the determined maximum cross-sectional dimension d2a of the first portion 114. The maximum cross-sectional dimensions of the embolization device, first portions, second portions, and anchor portions described herein refer to the dimension of the overall structure (e.g., from edge to edge along a plane), rather than the cross-sectional dimension of the wire, coil, or other elongated structure that is used to form the respective structure. In some examples, maximum cross-sectional dimension d2a of the first portion 114 is from about 10% to about 100% larger than maximum cross-sectional dimension d2b of each second portion 116, such as about 10% to 50% larger. When used to modify a numerical value, the term "about" is used herein may refer to the particular numerical value or nearly the value to the extent permitted by manufacturing tolerances. As an example, "about 10%" means "10% or nearly 10% to the extent permitted by manufacturing tolerances."

In some examples, the embolization devices may be configured or designed to be used with blood vessels of a particular size. Thus, in some cases, a clinician may evaluate the size of vessel to be embolized and then select a specific embolization device 100 configured for that particular size from among multiple embolization devices as described herein, with the devices varying in size according to a range of nominal vessel sizes. In some examples, embolization device 100 may be configured for a particular nominal vessel size. In such examples, the maximum cross-sectional dimension d2a may be slightly larger than the nominal vessel size. For example, the maximum cross-sectional dimension d2a may be about 1.1 to about 2 times (exactly 1.1 to 2 or within 10%) larger than the nominal vessel size, such as about 1.1 to about 1.4 times larger than the nominal vessel size or about 1.1 to about 1.3 times larger than the nominal vessel size. Too large of a maximum cross-sectional dimension d2a, such as larger than about 2 times larger than the nominal vessel size in some examples, may adversely impact the ability of the device 100 to form a loop within the vasculature when device 100 is deployed in the vasculature.

In some examples the maximum cross-sectional dimensions of the second portions 116 may be approximately the same (e.g., the same but for manufacturing tolerances) for each second portion 116, or the dimensions may vary between one second portion 116 and another second portion 116. In examples in which the maximum cross-sectional dimensions d2b are different due to, e.g., design and/or tolerances, each maximum cross-sectional dimension d2b can still be smaller than the maximum cross-sectional dimension d2a of the first portion 114. In some examples, the embolization device 100 is configured for a nominal vessel size and the maximum cross-sectional dimension d2b is equal to or slightly smaller than the nominal vessel size. For example, the maximum cross-sectional dimension d2b may be about 85% to about 100% of the nominal vessel size, or the nominal vessel size may be about 1.0 to about 1.1 times larger (e.g., exactly 1.0 to 1.1 or within 10%) than the maximum cross-sectional dimension d2b.

As described herein, example implantable embolization devices of the present technology can have a secondary or deployed configuration that includes multiple 3D structures. As illustrated in FIG. 1A, the embolization device 100 includes the first portion 114 with a 3D structure, and two second portions 116, each having a 3D structure. In some cases, 3D structures may also be referred to as complex shapes or configurations because the structures are formed from one or more loops positioned in various planes, unlike, e.g., a simpler structure such as a helical coil. In some examples the first portion 114 and/or second portions 116 may include a 3D structure that is approximately polyhedral in that each loop of the structure approximates one of the faces of a polyhedron. In the example of FIG. 1A, each of the 3D structures is formed from six loops that approximate the six face planes of a cube. In some examples a 3D structure may be cubic, tetrahedral, octahedral, or configured as any solid with sides shaped as a regular polygon.

In some examples, including some of those described herein, a 3D structure may be considered to approximate a sphere to a greater or lesser extent. In such cases the maximum cross-sectional dimension of each second portion is an outer diameter of the second portion. Further, the maximum cross-sectional dimension of a first portion is an outer diameter of the first portion.

As previously mentioned, the embolization devices of the present technology include an anchor portion 110 that is configured to anchor the embolization device 100 in the patient's vasculature. As an example, the anchor portion 110 may be configured to anchor the embolization device 100 along with the first deployed structure of the first portion 114. In the deployed configuration shown in FIG. 1A, the anchor portion 110 includes multiple loops, also referred to herein as anchor loops. The anchor loops can comprise a leading anchor loop 120 and a trailing anchor loop 122. In some embodiments the anchor portion 110 comprises more than two loops (e.g., 2.5 loops or more, 3 loops or more, etc.) or fewer than two loops (e.g., 1.75 loops or less, 1.50 loops or less, 1.25 loops or less, 1 loop or less, 0.75 loops or less, 0.50 loops or less, etc.).

In the example of FIG. 1A, the anchor portion 110 is connected to and continuous with the first portion 114 and is positioned on an opposite side of the first portion 114 from the second portions 116. In some examples, the anchor loops forming the anchor portion 110 form a helical structure, e.g., a spiral structure, configured to anchor the device 100 in the patient's vasculature. In some examples, the helical structure has a tapered configuration that increases in diameter from a leading loop 120 toward a trailing anchor loop 122 connected to the first portion 114, as shown in FIG. 1A. Alternatively, the helical structure of the anchor portion 110 may increase in diameter from the trailing anchor loop 122 towards leading loop 120. In examples in which anchor portion 110 has a tapered helical configuration, anchor portion 110 may define a conical spiral, e.g., a three-dimensional spiral that extends along the outer surface of an imaginary cone. The spiral may taper in a leading direction (away from the second portions 116) in some examples, as shown in FIG. 1A, or may taper in a proximal direction in other examples. In some examples, the smallest loop of the spiral is smaller than the intended vessel treatment range of the device so that this portion of the coil is assured to assume a deployed configuration, rather than an elongated configuration, when exiting the delivery system and deploying into the vasculature.

The loops of anchor portion 110 may not be closed loops, in which the loops of the coil are coplanar and a loop of a coil touches an adjacent loop in the "at rest" state (in which no compressive forces are applied to anchor portion 110 from a catheter, a blood vessel, or the like). Spacing the loops from each other in a longitudinal direction (e.g., proximal to distal direction or distal to proximal direction) may provide the loops with room to bend relative to each other and enable larger loops to decrease in cross-sectional dimension by spreading longitudinally when anchoring in a relatively small diameter vessel. In some examples, in its at-rest secondary configuration, in which no outward forces are being applied to the device 100 from a vessel wall or a catheter, the loops 120, 122 (and other loops, if present) may be separated from each other. In addition, in examples in which the loops 120, 122 (and other loops, if present) have different maximum (or greatest) cross-sectional dimensions (e.g., diameters) from each other, each loop of the anchor portion 110 may differ in a maximum cross-sectional dimension from an adjacent loop by a predetermined amount. For example, if the anchor portion 110 is defined by a primary structure having a cross-sectional dimension d1 (see FIG. 1B) of 0.25 mm, each loop may be 0.50 mm larger in diameter than an immediately distal (or proximal in some examples) loop. Other loop sizes may also be used in other examples.

In examples in which anchor portion 110 is closer to a leading end of the device 100 than the first portion 114 (e.g., a distalmost portion of the embolization device 100 or a proximalmost portion of the embolization device in other examples), the anchor portion 110 may be deployed from the catheter 200 before the first portion 114 and the second portions 116. For example, the leading anchor loop 120 of the anchor portion 110 may engage with the vessel wall and then subsequent loops of the anchor portion 110 may deform into a helix against the vessel wall, thereby potentially changing the shape of the anchor portion 110, e.g., from a conical spiral to a helix having more uniform loop sizes. The helical structure of the anchor portion 110 may enable the anchor portion 110 to engage the vessel wall at a distal end 200*b* of the catheter 200 (FIG. 2) and anchor at the treatment site as the rest of the embolization device 100 is deployed from the catheter 200.

While the first portion 114 is also configured to engage the vessel wall to create a fillable frame within the vasculature, the configuration (e.g., helical structure) of the anchor portion 110 and one or more stiffening features (detailed below) may enable the anchor portion 110 to be deployed more effectively than the first portion 114, which has smaller individual loops though a similar overall deployed outer diameter, thereby enabling the embolization device 100 to more effectively anchor within the blood vessel as the rest of the embolization device 100 is deployed from the catheter 200. The more effective anchoring of the embolization device 100 may enable the embolization device 100 to begin packing at or relatively close to the distal end 200*b* of the catheter 200, rather than sliding and/or whipping along the vessel wall without engaging the vessel wall. The structure of the embolization device 100 that enables it to begin packing at or relatively close to the distal end 200*b* of the catheter 200 (or other deployment location of a catheter) may provide a clinician with more precise control of the implanted position of the embolization device 100 in the body lumen of the patient, which may provide better treatment outcomes (e.g., in sacrificing a desired portion of a blood vessel).

In some examples, the anchor loops forming the helical structure of the anchor portion 110 may further assist in anchoring device 100 because the anchor loops may be configured to exert a larger radial force against the vessel wall compared to the first portion 114 and/or the second portions 116. For example, the helical loops may assist in penetrating the open space inside the vessel. Further, in examples in which the anchor portion 110 includes tapering loops, the various loop sizes defined by the anchor portion 110 may enable the anchor portion 110 to expand (as it is deployed from the catheter) to accommodate various vessel sizes (in cross-section). In these examples, embolization device 100 may be configured to accommodate clinician sizing preference (e.g., some clinicians may prefer a larger distal loop or a smaller distal loop based on their personal experience implanting embolization devices in patients), as well as vessel sizing uncertainty when selecting a particular size of the embolization device 100 to implant in a patient. In some cases, embolization device manufacturers may provide embolization devices in 1 millimeter increments corresponding to different vessel sizes (in cross-section), e.g., 4 mm vessels, mm vessels, and the like. In contrast to these devices configured for a specific vessel size, the embolization device 100 that is configured to accommodate a range of vessel sizes may better enable a clinician to select a device 100 that may provide a positive outcome for the patient by requiring a less accurate determination of the patient's vessel size.

In some examples, such as examples in which anchor portion 110 defines a conical spiral, the anchor portion 110 may also help to center embolization device 100 within a vessel wall, which may enable the embolization device 100 to achieve a higher packing density in some cases. A higher packing density may be more effective at stopping blood flow through the blood vessel within a given amount of time by providing a larger kinetic energy sink for the blood flow.

The anchor portion 110 may be formed from any suitable material. In some examples, the anchor portion 110 is formed from a different material (e.g., chemical composition) than the first portion 114 and/or the second portions 116. In other examples, the anchor portion 110 is formed from the same material as the first portion 114 and/or the second portions 116. For example, anchor portion 110 may be integrally formed with first and second portions 114, 116, and may be formed from the same material as first and second portions 114, 116. In any of these examples, the anchor portion 110 may be formed from a metal alloy, such as platinum tungsten (e.g., approximately 98% platinum and approximately 2% tungsten), platinum, iridium, or other suitable biocompatible materials. In addition, in some examples, the anchor portion 110 may be at least partially formed from a material that enables the anchor portion 110 to engage with the vessel wall (e.g., by friction fit or using an adhesive material) for a relatively short period of time that is less than the intended implant time of the embolization device 100.

In some examples, the embolization device 100 includes one or more first portions 114 only, or one or more first portions 114 and one or more second portions 116 (and no anchor portion 110). In such embodiments, the first portion 114 would include one or more of the stiffening features disclosed herein.

Figure 3:
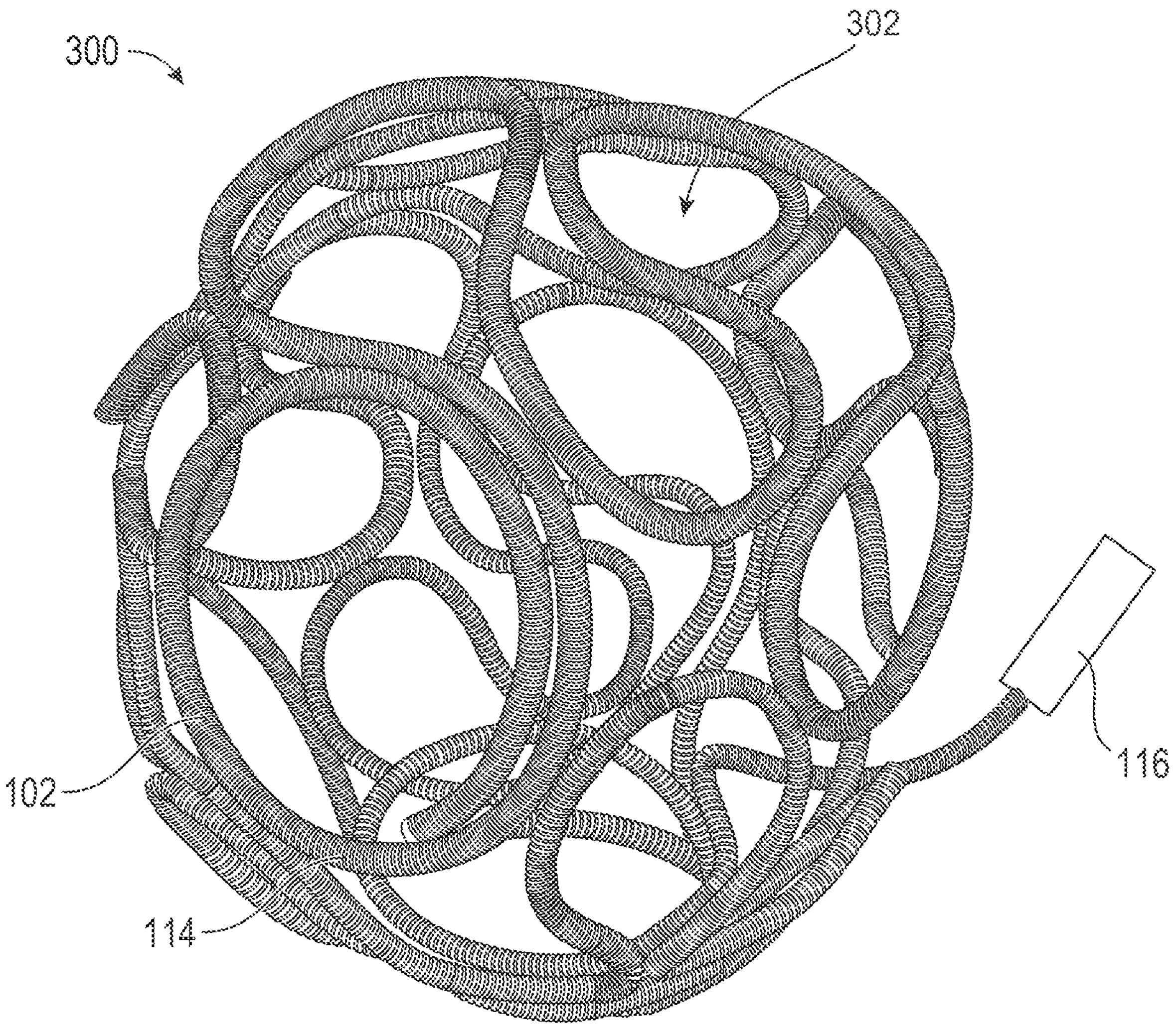
FIG. 3 is a perspective view illustrating an embolization device configured in accordance with several embodiments of the present technology.

The embolization devices described herein may also be useful for aneurysm occlusion. FIG. 3 shows a portion of an occlusive device 300 configured in accordance with the present technology. The occlusive device 300 can comprise a first portion 114 configured to frame and/or anchor the device within the aneurysm, and a second portion 116 (shown schematically) continuous with the first portion 114 that is configured to be positioned within an interior region 302 framed by the first portion 114. The second portion 116 is shown outside of the interior region 304 of the first portion 114 in FIG. 3 for ease of viewing the structure of the first portion 114. The occlusive device 300 can comprise a primary structure 102, as described above with respect to FIGS. 1A and 1B, that is shaped to produce the deployed configuration illustrated in FIG. 3. As described above, in some examples the primary structure 102 may be a wire or other filamentous material, or a tube. In some examples, including that shown in FIG. 3, the primary structure 102 may be a length of coiled material. For example, the primary structure 102 can be a length of coil formed from many windings or turns of a base structure, such as a wire or other suitable material. In some embodiments, the primary structure 102 defines a lumen extending therethrough. In some embodiments the device 300 can optionally include one or more occlusive members incorporated into and/or disposed on the base structure and/or primary structure 102. The occlusive members can be threads, strands, wires, coils, or other occlusive elements that increase the effective surface area of the device 100. In some embodiments the embolization device 100 does not include any occlusive members.

As shown in FIG. 3, the first portion 114 can be shape set to form a 3D shape when unconstrained, and when deployed in the aneurysm. For example, the first portion 114 can comprise a plurality of loops, each disposed at an angle relative to at least one of the other loops when the device 300 is in an expanded, unconstrained state. The loops can have the same diameter or different diameters. Together, the loops can enclose a globular shape when the device 300 is in an expanded, unconstrained state. In some embodiments, the first portion 114 of the embolization device 300 can include one or more of the stiffening features detailed herein. For example, one, some, or all of the loops can comprise one or more of the stiffening features described with respect to FIGS. 5-7. The second portion 116 can have any suitable structure for filling the interior region 302 of the first portion 114. In some embodiments, the second portion 116 comprises a length of the primary structure 102 that has not been shape set and has a more flexible, conformable configuration. In some embodiments, the second portion 116 can comprise a braid or other occlusive material that is joined to the proximal end of the first portion 114.

Figure 4A:
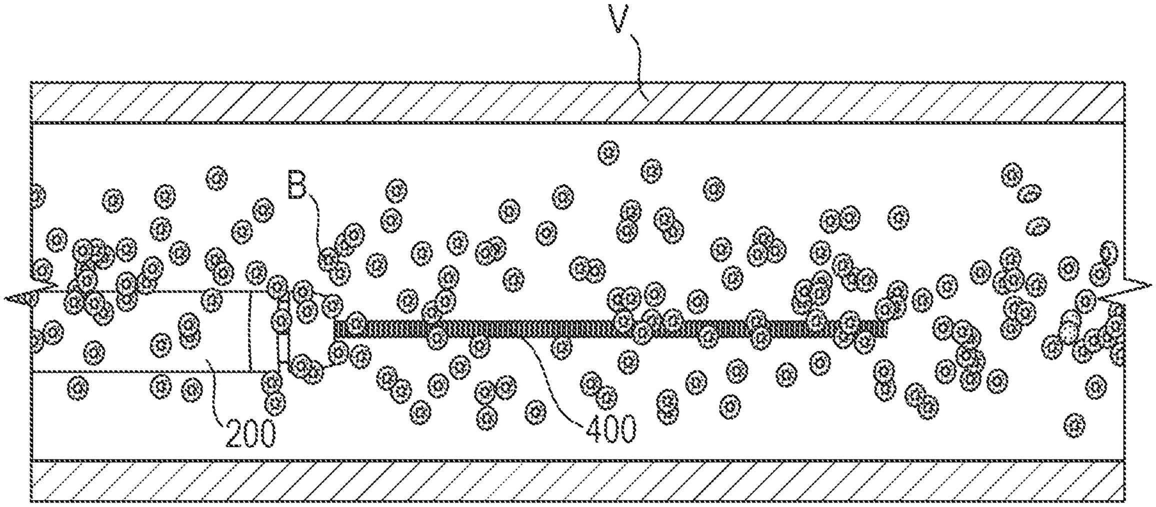
FIGS. 4A-4E show a method of deploying an embolization device configured in accordance with several embodiments of the present technology.
Figure 4B:
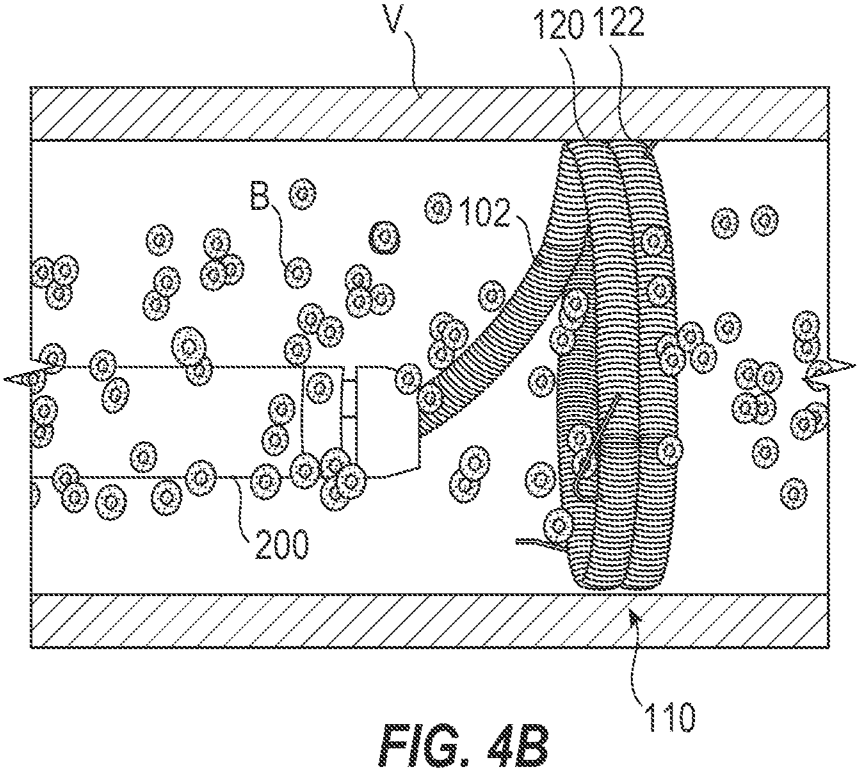
Figure 4C:
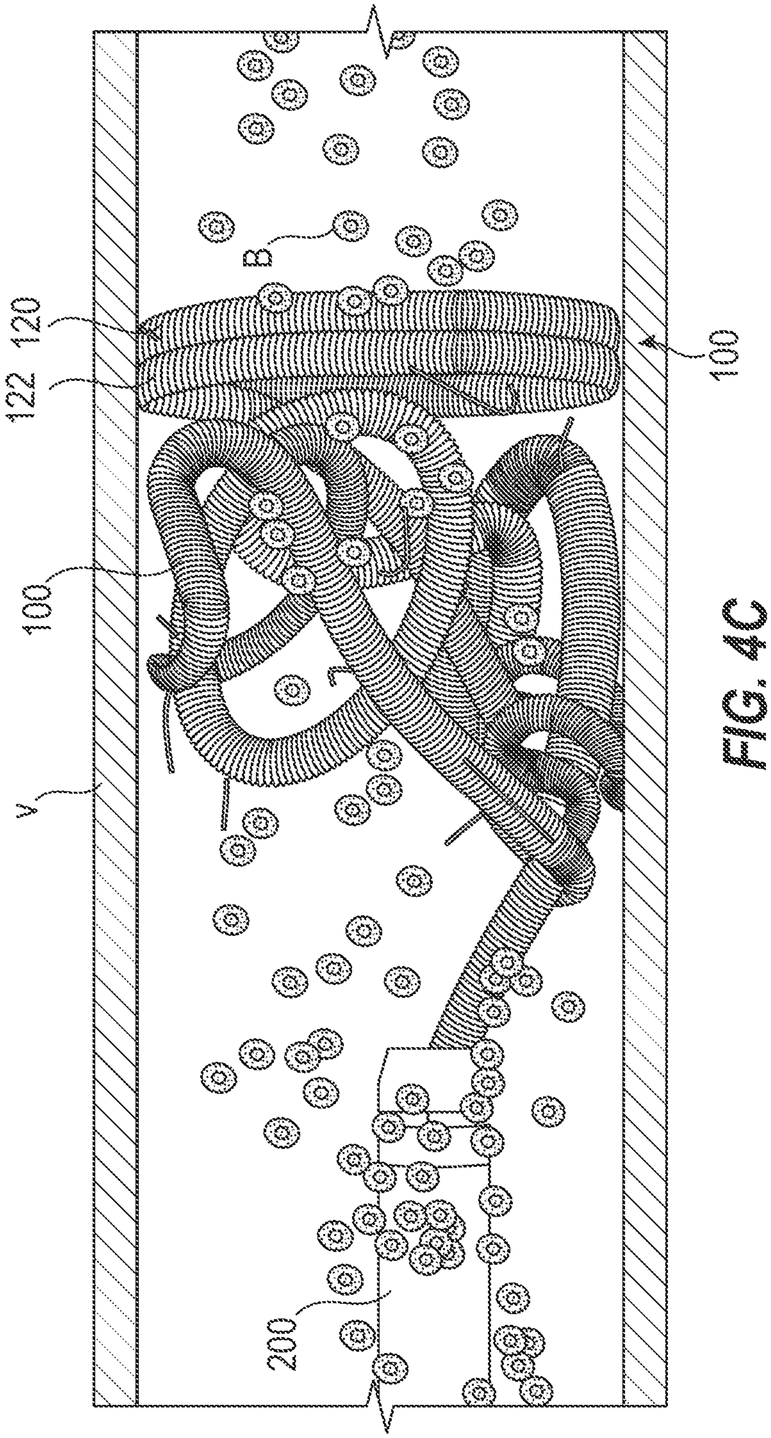
Figure 4D:
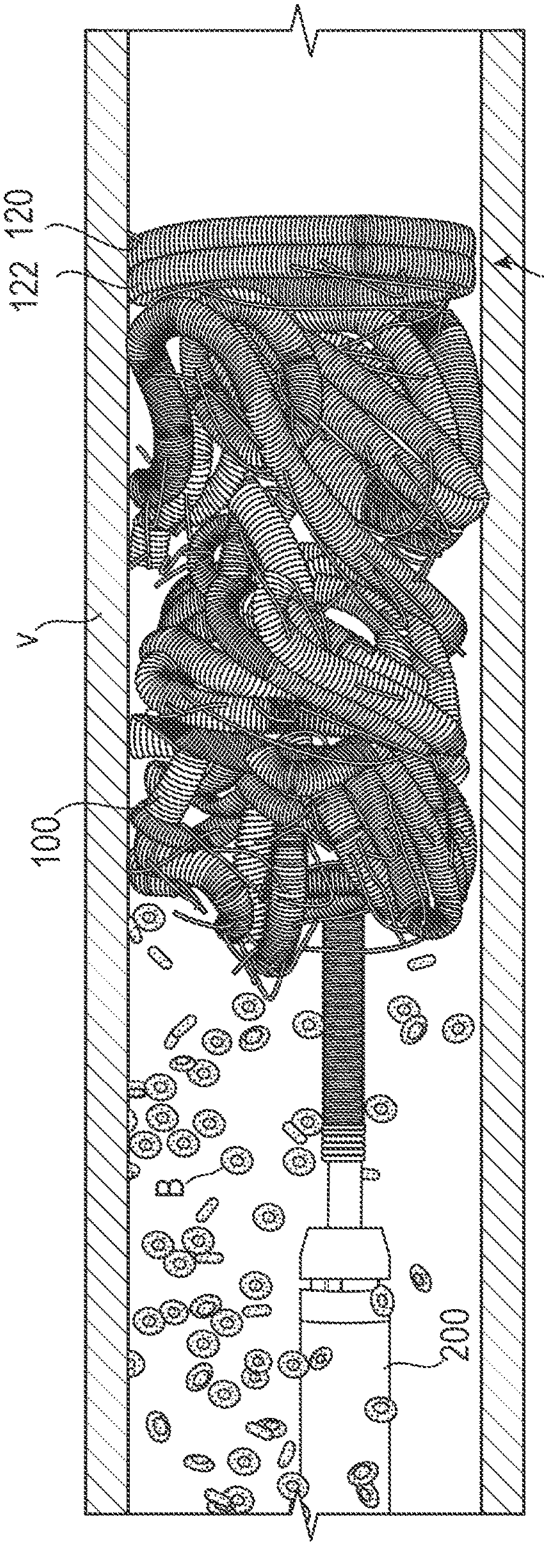
Figure 4E:
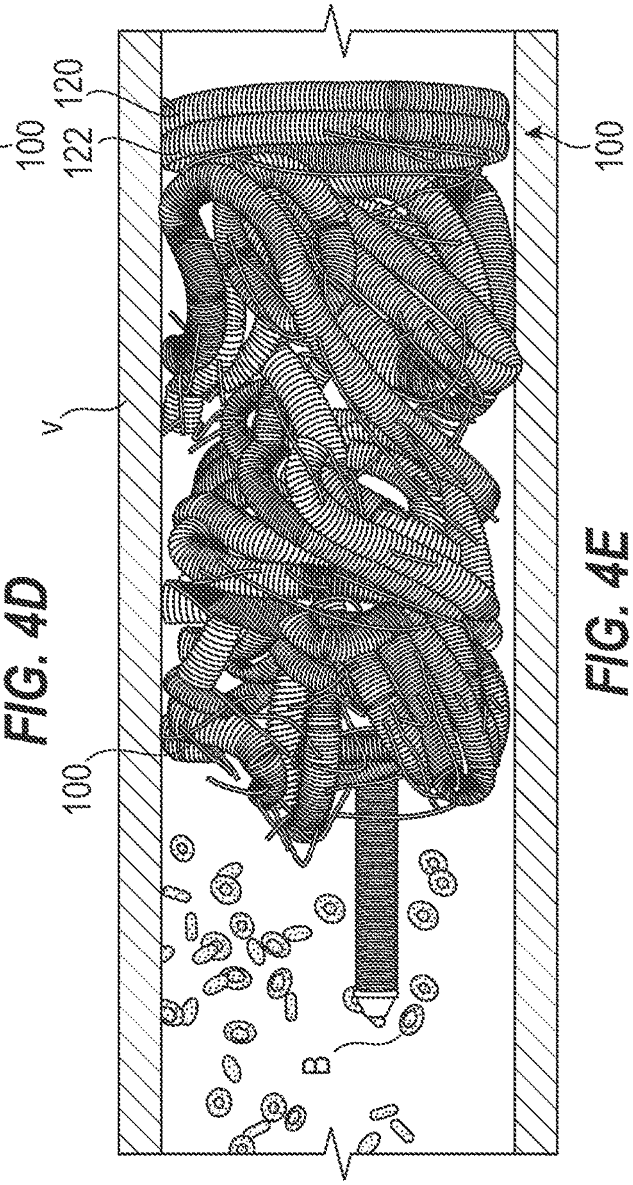

FIGS. 4A-4E show an example method of deploying the embolization device 100. As shown in FIG. 4A, the method includes introducing a catheter (such as catheter 200) into the vasculature of a patient and advancing the catheter 200 over a guidewire 400 to a treatment site within the patient's vasculature. Once the distal end 200*b* of the catheter 200 is at the desired position relative to the treatment site, a clinician may advance the embolization device 100 through the inner lumen 202 (FIG. 2) of the catheter 200 and deploy the embolization device 100 at the treatment site. For example, the clinician may apply a pushing force to the trailing end of the primary structure 102 (FIG. 2) using to expel the primary structure 102 from the inner lumen 202.

As the anchor portion 110 of the primary structure 102 and/or embolization device 100 comprises the leading end, the anchor portion 110 is the first portion of the embolization device 100 to be released into the vessel lumen. As depicted in FIG. 4B, upon release the primary structure 102 coils into the first and second anchor loops 120, 122 that are configured to anchor the primary structure 102 at the treatment site. For example, each of the first and second loops have a cross-sectional dimension that is slightly greater than the cross-sectional dimension of vessel V. As such, the first and second anchor loops 120, 122 press radially outwardly against the vessel wall V, thus securing the leading end of the embolization device 100 as the remainder of the primary structure 102 is released and the device 100 detached from the delivery system, as shown in FIGS. 4C-4E.

When deployed, the first portion 114 includes a 3D structure configured to engage with the blood vessel wall V and thereby help anchor the device 100 in the blood vessel V. The scaffold provided by the first portion 114 may be packed with the one or more second portions 116 of the embolization device 100. Configuring the first portion 114 to anchor within blood vessel V or at another vascular site may result in the first portion 114 being insufficient to pack the vascular site and reduce blood flow at the vascular site. The smaller deployed volume of each second portion 116 enables the one or more second portions 116 to fit within and pack the scaffolding defined by the first portion 114 to help obstruct blood vessel V. Thus, by including one or more second portions 116 in embolization device, the embolization device 100 can exhibit both effective anchoring at the vascular site and effective packing at the vascular site. As previously mentioned, however, in some embodiments the device 100 does not include different portions within the trailing portion.

When deploying an embolic device in a high-flow vessel, one challenge is getting the device to anchor or secure its position in the vessel prior to deploying additional loops of the device sufficient to slow and ultimately occlude blood flow in the vessel. In order to pack the loops densely into the vessel, the device must be very flexible. But to anchor effectively in the vessel as it is first being deployed, significantly higher coil stiffness may be required. As detailed below, the embolization devices of the present technology overcome these challenges by inclusion of one or more stiffening features at the distal end portion 100*b* of the device 100, such as along all or a portion of the anchor portion 110.

Figure 5:
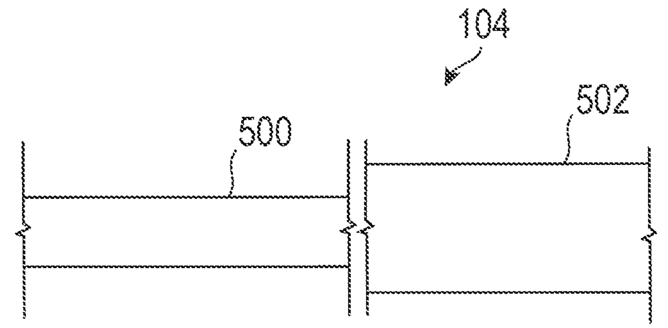
FIG. 5 is an enlarged view of a primary structure configured in accordance with several embodiments of the present technology.

According to some embodiments, the base structure 104 has a cross-sectional dimension d0 (FIG. 1B) that is greater near the leading end portion of the primary structure 102 than at the trailing end portion. FIG. 5, for example, shows an example a base structure 104 in the form of a wire having a first portion 500 with a first cross-sectional dimension and a second portion 502 with a second cross-sectional dimension greater than the first cross-sectional dimension. Accordingly, the portion of the primary structure 102 formed of the second portion 502 of the base structure 104 will be stiffer than the portion of the primary structure 102 formed of the first portion 500 of the base structure 104. Likewise, the portion of the embolization device 100 coinciding with the second portion 502 of the base structure 104 will be stiffer than the portion of the embolization device 100 coinciding with the first portion 500 of the base structure 104.

In some embodiments, a cross-sectional dimension of the base structure 104 can be greater along the length of the primary structure 102 that forms the anchor portion 110 of the embolization device 100 than along the length of the primary structure 102 that forms the trailing portion 112 of the embolization device 100. For example, in those embodiments in which the anchor portion 110 comprises one or more loops, a cross-sectional dimension of the base structure 104 can be greater along the one or more loops than along the length of the primary structure 102 that is proximal of the anchor portion 110. In some embodiments, the first anchor loop 120 and the second anchor loop 122 are formed of a length of the primary structure 102 that includes a length of the base structure 104 with the greater cross-sectional dimension. In some embodiments, less than all of the primary structure 102 forming the anchor portion 110 includes the base structure 104 with the greater cross-sectional dimension. For example, in some embodiments only the first anchor loop 120 comprises the portion of the base structure 104 with the greater cross-sectional dimension and the second anchor loop 122 comprises the portion of the base structure 104 with the lesser cross-sectional dimension. In certain cases, only the second anchor loop 122 comprises the portion of the base structure 104 with the greater cross-sectional dimension and the first anchor loop 120 comprises the portion of the base structure 104 with the lesser cross-sectional dimension. In some embodiments, the base structure 104 with the greater cross-sectional dimension extends along about 0.50 loops, 0.75 loops, 1.25 loops, 1.5 loops, 1.75 loops, 2 loops, 2.5 loops, 3 loops, 4 loops or 5 loops of the anchor portion 110. In some embodiments, all or a portion of the first portion 114 can include a length of the base structure 104 having the larger cross-sectional dimension.

In some aspects of the technology, the primary structure 102 can have a cross-sectional dimension d1 (FIG. 1B) that is greater near the leading end portion of the primary structure 102 than at the trailing end portion. For example, the primary structure 102 can be formed on a mandrel having a stepped or ramped cross-sectional dimension. Accordingly, the portion of the primary structure 102 having the greater cross-sectional dimension will be stiffer than the portion of the primary structure 102 with the lesser cross-sectional dimension. Likewise, the portion of the embolization device 100 coinciding with the portion of the primary structure 102 with the larger cross-sectional dimension will be stiffer than the portion of the embolization device 100 coinciding with the portion of the primary structure 102 having the lesser cross-sectional dimension.

In some embodiments, a cross-sectional dimension of the primary structure 102 can be greater along the portion of its length forming the anchor portion 110 of the embolization device 100 than along the portion of its length forming the trailing portion 112 of the embolization device 100. For example, in those embodiments in which the anchor portion 110 comprises one or more loops, a cross-sectional dimension of the primary structure 102 can be greater along the one or more loops than along the length of the primary structure 102 that is proximal of the anchor portion 110. In some embodiments, the first anchor loop 120 and the second anchor loop 122 are formed of a length of the primary structure 102 having the greater cross-sectional dimension. In some embodiments, less than all of the primary structure 102 forming the anchor portion 110 has the greater cross-sectional dimension. For example, in some embodiments only the first anchor loop 120 comprises the portion of the primary structure 102 with the greater cross-sectional dimension and the second anchor loop 122 comprises the portion of the primary structure 102 with the lesser cross-sectional dimension. In certain cases, only the second anchor loop 122 comprises the portion of primary structure 102 with the greater cross-sectional dimension and the first anchor loop 120 comprises the portion of the primary structure 102 with the lesser cross-sectional dimension. In some embodiments, the primary structure 102 with the greater cross-sectional dimension extends along about 0.50 loops, 0.75 loops, 1.25 loops, 1.5 loops, 1.75 loops, 2 loops, 2.5 loops, 3 loops, 4 loops or 5 loops of the anchor portion 110.

Figure 6:
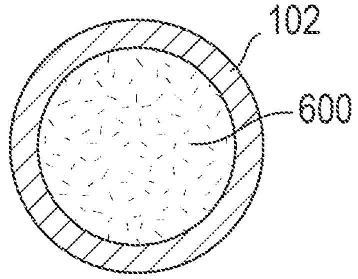
FIG. 6 is an axial cross-sectional view of a primary structure configured in accordance with several embodiments of the present technology.

According to some aspects of the technology, one or more portions of the primary structure 102 can be filled with a filler material to increase the stiffness of the primary structure 102 along those portions. FIG. 6, for example, is an axial cross-sectional view of a primary structure 102 having a filler material 600 disposed within a lumen of the primary structure 102. The filler material 600 can be positioned in the lumen of the primary structure 102 prior to implantation of the embolization device 100. For example, in some methods of manufacture, the primary structure 102 is shape set in a desired secondary configuration (such as that shown in FIGS. 1A and 3), and then the filler material 600 is added to the lumen of the already-shaped primary structure 102. The filler material 600 can be a flowable substance that cures and/or solidifies after injection into the primary structure lumen. In some embodiments, the filler material 600 is added during or after implantation of the device 100.

In some embodiments, the filler material 600 extends along a length of the primary structure 102 that forms the anchor portion 110 and is not disposed along the length forming the trailing portion 112. For example, in those embodiments in which the anchor portion 110 comprises one or more loops, the filler material 600 can be disposed along a length of the primary structure 102 that forms the one or more loops. In some embodiments, the filler material 600 is disposed along a length of the primary structure 102 that forms the first anchor loop 120 and the second anchor loop 122. In some embodiments, less than all of the primary structure 102 forming the anchor portion 110 includes the filler material 600. For example, in some embodiments only the first anchor loop 120 includes the filler material 600 and the second anchor loop 122 does not include any filler material 600. In certain cases, only the second anchor loop 122 includes the filler material 600 and the first anchor loop 120 does not include the filler material 600. In some embodiments, the portion of the primary structure 102 including the filler material 600 extends along about 0.50 loops, 0.75 loops, 1.25 loops, 1.5 loops, 1.75 loops, 2 loops, 2.5 loops, 3 loops, 4 loops or 5 loops of the anchor portion 110.

Figure 7:
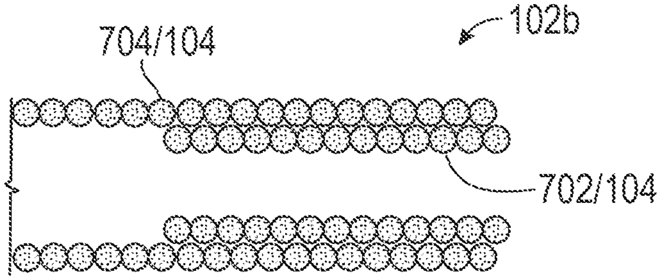
FIG. 7 shows an end portion of a primary structure configured in accordance with several embodiments of the present technology.

In various embodiments of the present technology, the primary structure 102 can comprise two or more coiled layers. FIG. 7, for example, shows the leading end 102*b* of a primary structure 102 configured in accordance with several embodiments of the present technology. The primary structure 102 comprises an inner wind 702 and an outer wind 704 surrounding the inner wind 702. The inner and outer winds 702, 704 can be different lengths of the same base structure 104 that are wound in opposite directions (as discussed below with reference to FIGS. 8A-8C), or may be formed of different base structures. In the latter embodiments, the inner wind 702 can be a coil that is formed of a different base structure 104 than the outer wind 704 and inserted into the lumen of the outer wind 704. The inner and outer winds 102, 104 can then be joined together. The joining can be done by welding, soldering, adhesive, and/or mechanical locking. In any case, the inner and outer winds 702, 704 can have the same thickness (equivalent to the cross-sectional dimension of the base structure 104 forming the wind) or different thicknesses.

In some embodiments, the portion of the primary structure 102 having the multi-layer sidewall coincides with the anchor portion 110 and the portion of the primary structure 102 coinciding with the trailing portion 112 has only a single layer sidewall. For example, in those embodiments in which the anchor portion 110 comprises one or more loops, the portion of the primary structure 102 having the multi-layer sidewall coincides with a length of the primary structure 102 that forms the one or more loops. In some embodiments, the portion of the primary structure 102 having the multi-layer sidewall forms the first anchor loop 120 and the second anchor loop 122. In some embodiments, less than all of the primary structure 102 forming the anchor portion 110 includes the multi-layer sidewall. For example, in some embodiments only the first anchor loop 120 includes the multi-layer sidewall and the second anchor loop 122 is a single layer sidewall. In certain cases, only the second anchor loop 122 includes the multi-layer sidewall and the first anchor loop 120 is a single-layer sidewall. In some embodiments, the portion of the primary structure 102 having the multi-layer sidewall extends around 0.50 loops, 0.75 loops, 1.25 loops, 1.5 loops, 1.75 loops, 2 loops, 2.5 loops, 3 loops, 4 loops or 5 loops of the anchor portion 110. The overlapping or multi-layer portion of the primary structure 102 can have a length along the longitudinal axis L1 of the primary structure 102 (see FIG. 1B) of about 4.5 mm to about 500 mm. In some embodiments, the inner and outer winds 702, 704 have the same pitch. In other embodiments, the inner and outer winds 702, 704 have different pitches.

Figure 8A:
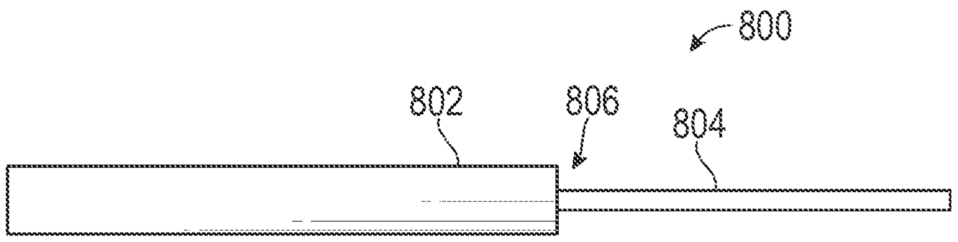
FIGS. 8A-8C depict a method of making the primary structure shown in FIG. 7 in accordance with several embodiments of the present technology.
Figure 8B:
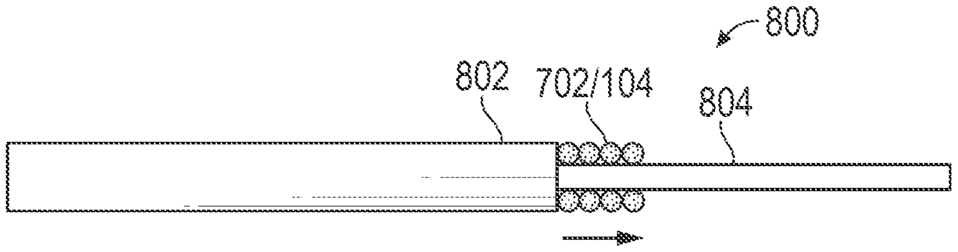
Figure 8C:
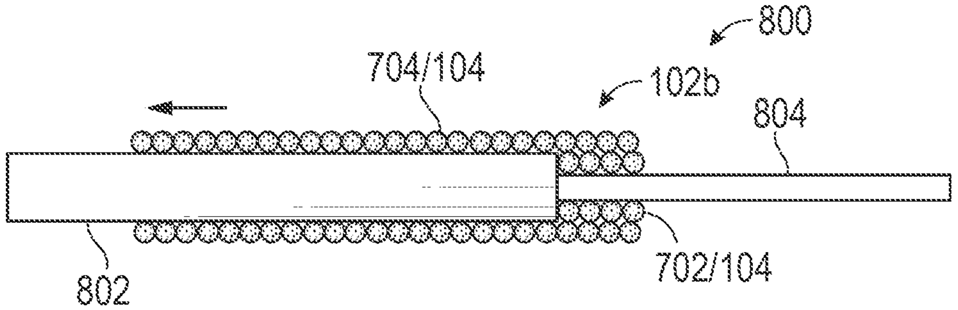

FIGS. 8A-8C depict an example method of making the primary structure 102 shown in FIG. 7 in accordance with several embodiments of the present technology. As shown in FIG. 8A, the method can include obtaining a mandrel 800 having a first portion 802 with a first cross-sectional dimension and a second portion 804 having a second cross-sectional dimension less than the first cross-sectional dimension. The mandrel 800 can further include a stepped portion 906 where the first portion 802 meets the second portion 804 and that has a length equivalent to a difference between the first and second cross-sectional dimensions. In some embodiments, it may be beneficial to use a mandrel having a stepped portion with a length that is substantially the same as the cross-sectional dimension of the selected base structure. As shown in FIG. 8B, winding of the base structure 104 can start at the stepped portion 806 (not labeled in FIG. 8B). From there, the base structure 104 can be wound around the second, smaller portion 804 of the mandrel 800 in a direction away from the first portion 802 (denoted by the arrow) to form the inner wind 702. As shown in FIG. 8C, after the base structure 104 has been wound a sufficient length (corresponding to the length of the multi-layer region), the base structure 104 can then be wound over the inner wind 702 in the opposite direction, towards and eventually over the first portion 802 of the mandrel 800 (denoted by the arrow) to form the outer wind 704. Winding of the outer wind 704 can continue until the desired length of the primary structure 102 is wound. Although FIGS. 8A-8C show a relatively short length of the inner wind 702, this is for ease of illustration. It will be appreciated that the inner wind 702 can extend for a length sufficient to impart the desired rigidity to the distal portion 100*b* of the embolization device 100, as described herein.

The primary structure 102 of the present technology can include one, some, or all of the stiffening features described herein. For example, in some embodiments the distal portion and/or anchor portion 110 of the primary structure 102 can include at least one of a portion of the base structure 104 with the larger cross-sectional dimension, a portion of the primary structure 102 with the larger cross-sectional dimension, the filler material 600, the multi-layer sidewall, or others. When multiple stiffening features are utilized, the stiffening features can overlap along the longitudinal axis L1 (FIG. 1B) of the primary structure 102, be longitudinally adjacent and abut one another, or be spaced apart along the longitudinal axis. For example, in some embodiments all or a portion of the anchor portion 110 can comprise a filler material 600 and a portion of the primary structure 102 formed of the base structure 104 with the larger cross-sectional dimension. In some embodiments all or a portion of the anchor portion 110 can comprise a filler material 600 and a multi-layer portion of the primary structure 102. According to certain embodiments, all or a portion of the anchor portion 110 can comprise a multi-layer portion of the primary structure 102 and a portion of the primary structure 102 formed of the base structure 104 with the larger cross-sectional dimension. In various embodiments, all or a portion of the anchor portion 110 can comprise a filler material 600, a multi-layer portion of the primary structure 102, and a portion of the primary structure 102 formed of the base structure 104 with the larger cross-sectional dimension. Use of multiple stiffening features can provide enhanced rigidity as compared to the use of a single stiffening feature.

The embolization device 100 as well as other embolization devices described herein may be formed using any suitable technique, such as by using a mandrel that includes different posts extending therefrom to define different parts of embolization device 100. The resulting path of the primary structure 102 (and thus the complex shape of the embolization device 100) is defined, at least in part, by the position of the posts along the length and circumference of the mandrel.

CONCLUSION

Although many of the embodiments are described above with respect to devices, systems, and methods for embolizing blood vessels and aneurysms, the technology is applicable to other applications and/or other approaches, such as occlusion of body lumens outside of the vasculature. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-8C.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An embolization device configured to be positioned within a body lumen of a patient, the embolization device comprising:

an elongated primary structure formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the primary structure has a first length corresponding to the trailing portion and a second length corresponding to the anchor portion, and wherein a sidewall of the primary structure comprises a first number of coil layers along the first length and a second number of coil lavers along the entire second length, the second number greater than the first number, and wherein the wire comprises a first wire length comprising a first cross-sectional dimension and a second wire length comprising a second cross-sectional dimension greater than the first cross-sectional dimension, each of the first and second cross-sectional dimensions measured perpendicular to a longitudinal axis of the wire, and wherein the first length of the wire extends along at least a portion of the first length of the primary structure and the second length of the wire extends along at least a portion of the second length of the primary structure.

2. The embolization device of claim 1, wherein the second length of the wire extends along the entire portion of the second length of the primary structure.

3. The embolization device of claim 1, wherein the anchor portion comprises a first loop and a second loop contiguous with the first loop, and wherein the second length of the wire extends along one or both of the first loop and the second loop.

4. The embolization device of claim 1, wherein the embolization device is configured to be positioned within a blood vessel.

5. The embolization device of claim 1, wherein the primary structure defines a lumen extending therethrough.

6. The embolization device of claim 1, wherein the embolization device is configured to be positioned within an aneurysm.

7. The embolization device of claim 1, wherein the primary structure defines a lumen extending therethrough, and wherein the primary structure comprises a filler material disposed within the lumen along at least a portion of the second length.

8. The embolization device of claim 1, wherein the trailing portion has a first portion configured to deploy to a maximum cross-sectional dimension and a second portion configured to deploy to a maximum cross-sectional dimension different than the maximum cross-sectional dimension of the first portion.

9. The embolization device of claim 8, wherein the first portion of the trailing portion is continuous with the anchor portion.

10. The embolization device of claim 9, wherein the maximum cross-sectional dimension of the first portion is greater than the maximum cross-sectional dimension of the second portion.

11. The embolization device of claim 1, wherein the trailing portion forms at least one loop when the embolization device is implanted at the treatment site.

12. The embolization device of claim 1, wherein the anchor portion is configured to define a conical spiral in a deployed state.

13. The embolization device of claim 1, wherein the anchor portion is configured to exert a larger radial force against the vessel wall compared to the trailing portion when embolization device is implanted at the treatment site.

14. An embolization device configured to be positioned within a body lumen of a patient, the embolization device comprising:

an elongated primary structure formed of a coiled wire, wherein the primary structure forms a secondary structure when unconstrained in which the primary structure forms an anchor portion and a trailing portion, and wherein:

the anchor portion comprises at least one loop configured to be in contact with and press radially outwardly against an inner surface of the body lumen at a treatment site such that the anchor portion is configured to anchor the embolization device at the treatment site, and the trailing portion is configured to fill space in the body lumen to reduce or block flow into and/or through the body lumen, wherein the trailing portion is more flexible than the anchor portion, wherein the primary structure has a first length corresponding to the trailing portion and a second length corresponding to the anchor portion, and wherein the wire forms a single coil layer along the first length and doubles back on itself to form two coil layers along the second length, and wherein the wire comprises a first wire length comprising a first cross-sectional dimension and a second wire length comprising a second cross-sectional dimension greater than the first cross-sectional dimension, each of the first and second cross-sectional dimensions measured perpendicular to a longitudinal axis of the wire, and wherein the first length of the wire extends along at least a portion of the first length of the primary structure and the second length of the wire extends along at least a portion of the second length of the primary structure.

15. The embolization device of claim 14, wherein the second length of the wire extends along the entire portion of the second length of the primary structure.

16. The embolization device of claim 14, wherein the anchor portion comprises a first loop and a second loop contiguous with the first loop, and wherein the second length of the wire extends along one or both of the first loop and the second loop.

17. The embolization device of claim 14, wherein the embolization device is configured to be positioned within a blood vessel.

18. The embolization device of claim 14, wherein the primary structure defines a lumen extending therethrough.

19. The embolization device of claim 14, wherein the embolization device is configured to be positioned within an aneurysm.

20. The embolization device of claim 14, wherein the trailing portion has a first portion configured to deploy to a maximum cross-sectional dimension and a second portion configured to deploy to a maximum cross-sectional dimension different than the maximum cross-sectional dimension of the first portion.

* * * * *